(12) United States Patent
Brunet et al.

(10) Patent No.: US 10,736,864 B2
(45) Date of Patent: Aug. 11, 2020

(54) IMMUNOTHERAPEUTIC AGENT

(71) Applicants: Immodulon Therapeutics Limited, Uxbridge (GB); The Regents of the University of Colorado, a Body Corporate, Denver, CO (US)

(72) Inventors: Laura Rosa Brunet, Uxbridge (GB); Christopher A. Lowry, Boulder, CO (US)

(73) Assignees: IMMODULON THERAPEUTICS LIMITED, Uxbridge (GB); THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 0 days.

(21) Appl. No.: 16/270,284

(22) Filed: Feb. 7, 2019

(65) Prior Publication Data
US 2019/0167623 A1  Jun. 6, 2019

Related U.S. Application Data

(62) Division of application No. 15/856,532, filed on Dec. 28, 2017, now abandoned.

(60) Provisional application No. 62/440,353, filed on Dec. 29, 2016.

(51) Int. Cl.
*A61K 31/201* (2006.01)
*A61P 31/00* (2006.01)
*A61K 9/00* (2006.01)
*A61K 31/231* (2006.01)

(52) U.S. Cl.
CPC .......... *A61K 31/201* (2013.01); *A61K 9/0019* (2013.01); *A61K 31/231* (2013.01); *A61P 31/00* (2018.01)

(58) Field of Classification Search
None
See application file for complete search history.

(56) References Cited

U.S. PATENT DOCUMENTS 7,569,213 B2    8/2009   Brunet et al.
2018/0185317 A1  7/2018   Brunet et al.

FOREIGN PATENT DOCUMENTS

WO   WO 2001/19356   *  3/2001   ............. A61K 31/00

OTHER PUBLICATIONS

Druml et al (JPEN J Parenter Enteral Nutr 22:217-223, 1998—Abstract only) (Year: 1998).*
Official Action for U.S. Appl. No. 15/856,532, dated Aug. 8, 2018, 8 pages.

* cited by examiner

*Primary Examiner* — Craig D Ricci
(74) *Attorney, Agent, or Firm* — Berg Hill Greenleaf Ruscitti LLP (57) ABSTRACT

Compounds for use in the treatment of sepsis and/or the prevention or treatment of post-sepsis syndrome.

3 Claims, 8 Drawing Sheets

IMMUNOTHERAPEUTIC AGENT

CROSS REFERENCE TO RELATED APPLICATION

This application is a divisional of U.S. patent application Ser. No. 15/856,532, filed on Dec. 28, 2017, which claims the benefit of U.S. Provisional Patent Application Ser. No. 62/440,353 filed Dec. 29, 2016, the disclosure of which is incorporated herein by reference.

FIELD OF THE INVENTION

The present invention provides compounds for use in the treatment of sepsis and/or the prevention or treatment of post-sepsis syndrome.

BACKGROUND OF THE INVENTION

Sepsis, a potentially life-threatening condition triggered by an infection or injury, is the result of an overwhelming inflammatory host response to bacterial infection. During sepsis, the body's immune system is dysregulated as it tries to fight an infection, and this can reduce blood supply to vital organs such as the brain, heart and kidneys which can cause multiple organ failure and ultimately death.

It had long been believed that sepsis merely represented an exaggerated, hyperinflammatory response that led to inflammation-induced organ injury, but recent data indicate that substantial heterogeneity exists in septic patients' inflammatory response, with some appearing immuno-stimulated, whereas others appear suppressed. It is clear that multiple pathological mechanisms contribute to sepsis.

The current view of sepsis includes the concept of a Systemic Inflammatory Response Syndrome (SIRS) that has been induced by an infection. Recent data suggests that an appropriate inflammatory response allows elimination of invading microorganisms without causing damage to tissues, organs, or other systems. However, dysregulated inflammation prevents this elimination and allows sepsis to occur by permitting the physiological alterations that manifest as the SIRS. Macrophage activation is thought to play a central role in the initiation and propagation of the systemic inflammatory response.

Inflammatory cells, and monocytes and macrophages in particular, play a central role in the response to invading pathogens and in the pathogenesis of sepsis (Van Amersfoort, E. S. et al. (2003) Clin. Microbiol. Rev. 16(3):379-414). Macrophages in particular have been directly implicated in numerous pathogenic mechanisms that cause organ damage in the septic patient, including for example cardiac infiltration leading to heart disease (Cuenca, J. et al. (2006) Am. J. Pathol. 169(5):1567-1576)

Despite intense efforts, sepsis remains a serious clinical problem despite improvements in critical care management. Despite widespread availability of antibacterial therapies and the development of improved immunotherapies, there remains a need to improve the efficacy of treatment of sepsis.

SUMMARY

The present invention provides compositions for the treatment of sepsis. More specifically the invention provides synthetic fatty acids and mono-, di- and tri-esters of the fatty acid and 1,2,3-propanetriol, which are useful in treating sepsis.

The present invention is based on the surprising finding by the inventors that previously described esters of 1,2,3-propanetriol with one or more $C_{11}$ to $C_{24}$ fatty acids, having at least one fatty acid having only one double bond at the C10-C11 position prevented lipopolysaccharide-stimulated secretion of the proinflammatory cytokine IL-6 from freshly isolated peritoneal macrophages. Such compounds downregulate expression of proinflammatory cytokine and chemokine ligand mRNAs in activated macrophages and inhibit the pro-inflammatory signalling of activated macrophages in vitro. Compounds of the invention are therefore useful in inhibiting the proinflammatory cascade that contributes to the pathology of sepsis.

In a first aspect, the invention provides an ester of 1,2,3-propanetriol with one or more fatty acids of at least C11, wherein at least one fatty acid has a double bond at the C10-C11 position, for use in the treatment of sepsis.

The compounds of the first aspect can be used to inhibit proinflammatory signalling by activated macrophages in sepsis, and this can allow effective treatment of infection underlying the sepsis while preventing the organ damage that it produces.

In a second aspect, the invention provides a fatty acid of at least C11 comprising a double bond between C10 and C11 for use in the treatment of sepsis or and/or the prevention or treatment of post-sepsis syndrome.

The compounds of the second aspect can be used to inhibit proinflammatory signalling by activated macrophages in sepsis, and this can allow effective treatment of infection underlying the sepsis while preventing the organ damage that it produces.

In a third aspect, the invention provides a method of treating sepsis or chronic neuropathic pain comprising administration of a compound which is an ester of 1,2,3-propanetriol and one or more fatty acids of at least C11, wherein at least one fatty acid has a double bond at the C10-C11 position.

The method of the third aspect can be used to inhibit proinflammatory signalling by activated macrophages and delay the development of sepsis, and this opens a time window to allow effective treatment of infection underlying the sepsis while preventing the organ damage that it produces.

In a fourth aspect, the invention provides a method of treating sepsis and/or of preventing or treating post-sepsis syndrome, comprising administration of a fatty acid of at least C11 comprising a double bond between C10 and C11.

The method of the fourth aspect can be used to inhibit proinflammatory signalling by activated macrophages and delay the development of sepsis, and this opens a time window to allow effective treatment of infection underlying the sepsis while preventing the organ damage that it produces.

DESCRIPTION OF THE FIGURES

The invention is described herein with reference to the following Figures.

FIG. 1A shows that compared to vehicle-treated control mice, subcutaneous treatment with whole *M. vaccae* or lipid fraction 148.2 reduced the total number of cells recovered in the bronchoalveolar lavage (BAL) fluid of allergic mice challenged with ovalbumin.

Allergic mice were treated with vehicle (white bars) or with 0.1 mg of a heat-killed preparation of *M. vaccae* (Mva; black bars) or with 2 doses of lipid fraction 148.2 (grey bars). FIG. 1B shows that compared to vehicle-treated control mice, mice treated with *M. vaccae* or one of two doses of lipid fraction 148.2 had reduced numbers of eosinophils (EOS) and macrophages (MQO) recovered in the BAL fluid of allergic mice challenged with ovalbumin. Data are expressed as mean±SEM of 6-8 mice per group. These results are representative of two separate experiments. *p<0.05 relative to vehicle-treated controls as determined by ANOVA analysis. Abbreviations: EOS, eosinophils; MQ, macrophages; NEUTS, neutrophils;

FIG. 2 shows data obtained from Experiment 3 showing that the synthetic triglyceride, 1,2,3-tri[Z-10-hexadecenoyl] glycerol, reduces bronchopulmonary inflammation. Treatment with a synthetic triglyceride originally isolated and purified from *M. vaccae* reduces the severity of pulmonary allergic inflammation. Allergic mice were treated with vehicle (white bars), with 0.1 mg of heat-killed *M. vaccae* (black bars) or with a 5 µg dose of the synthetic triglyceride 1,2,3-tri[Z-10-hexadecenoyl]glycerol (gray bars). Compared to control mice, subcutaneous treatment with whole heat-killed *M. vaccae* reduced the numbers of eosinophils (EOS) and macrophages (MQO) recovered in the bronchoalveolar lavage (BAL) fluid of allergic mice challenged with ovalbumin, while synthetic triglyceride 1,2,3-tri[Z-10-hexadecenoyl]glycerol reduced the numbers of eosinophils (EOS) recovered in the BAL fluid of these mice. Data are expressed as mean±SEM of 6-8 mice per group. These results are representative of two separate experiments. *p<0.05 when compared to treatment with vehicle as determined by ANOVA analysis. Abbreviations: EOS, eosinophils; MQ, macrophages; NEUTS, neutrophils;

FIG. 3A shows the levels of interleukin (IL)-5 and IL-10 measured in the bronchoalveolar lavage (BAL) fluid of allergic mice treated with buffer (white bars), with 0.1 mg of a heat-killed preparation of *M. vaccae* (black bars) or with a 5 µg dose of the synthetic triglyceride 1,2,3-tri[Z-10-hexadecenoyl]glycerol (gray bars). Treatment with 1,2,3-tri [Z-10-hexadecenoyl]glycerol reduced IL-5 levels and increased IL-10 levels. FIG. 3B shows the levels of IL-5 and IL-10 measured in the supernatant of splenocytes stimulated in vitro with ovalbumin. Splenocytes of mice treated with 1,2,3-tri[Z-10-hexadecenoyl]glycerol produced less IL-5 and more IL-10. Data are expressed as mean±SEM from pooled spleens of 6-8 mice per group. These results are representative of two separate experiments.

FIG. 4D shows a control performed in the presence or absence of LPS. Shown are the effects of incubation with 10(Z)-hexadecenoic acid for 1 h prior to treatment with 1 µg/mL LPS, replicating the effects shown in FIGS. 4A-4C. Data for effects of 10(Z)-hexadecenoic acid in the absence of LPS are not shown as all values were 0, indicating that 10(Z)-hexadecenoic acid by, itself, has no detectable effect on IL-6 secretion from macrophages.

FIG. 5 shows a macrophage cell viability assay. Sulforhodamine B (SRB) was used to assess cytotoxic effects of various concentrations of 10(Z)-hexadecenoic acid (10 µM, 50 µM, 100 µM, 250 µM, 500 µM, 1000 µM) after 0, 6, 12, 24, 48, and 72 h of incubation with freshly isolated murine peritoneal macrophages. Percent control growth is expressed as % viability and is a ratio of the amount of growth that occurred with treatment over the amount of growth that occurred in media. One hundred percent indicates no differences in cell growth between treatment and media, whereas values below 100% indicate that growth was impaired with treatment. Data are expressed as mean±SEM of 3-7 mice per condition.

DETAILED DESCRIPTION

The present invention provides lipid compounds or fatty acids for the treatment of sepsis and the prevention or treatment of post-sepsis syndrome. More specifically the lipid compounds for the treatment of sepsis are fatty acids, or mono-, di- and tri-esters of the fatty acid and 1,2,3-propanetriol. The lipids or fatty acids can be synthesized in vitro. Alternatively, the lipid compound or fatty acid may be derived or extracted from *Mycobacterium* vaccae. *M. vaccae* is sometimes referred to as DAR-901 and a suitably exemplary strain is deposited under the NCTC accession number NCTC 11659.

In another aspect of the invention, the lipid compound or fatty acid may be derived or extracted from a *Mycobacterium* selected from the list including *M. vaccae, M. thermoresistibile, M. flavescens, M. duvalii, M. phlei, M. obuense, M. parafortuitum, M. sphagni, M. aichiense, M. rhodesiae, M. neoaurum, M. chubuense, M. tokaiense, M. komossense, M. aurum, M. indicus pranii, M. tuberculosis, M. microti; M. africanum; M. kansasii, M. marinum; M. simiae; M. gastri; M. nonchromogenicum; M. terrae; M. triviale; M. gordonae; M. scrofulaceum; M. paraffinicum; M. intracellulare; M. avium; M. xenopi; M. ulcerans; M. diernhoferi, M. smegmatis; M. thamnopheos; M. flavescens; M. fortuitum; M. peregrinum; M. chelonei; M. paratuberculosis; M. leprae; M. lepraemurium* and combinations thereof.

The term "sepsis" in the context of the present invention is understood to mean a life-threatening condition that arises when the body's response to infection injures its own tissues and organs. Common signs and symptoms include fever, increased heart rate, increased breathing rate and confusion. There may also be symptoms related to a specific infection, such as a cough with pneumonia, or painful urination with a kidney infection. In the very young, old, and people with weakened immune systems, there may be no symptoms of a specific infection and body temperature may be normal or lower than normal rather than high. Severe sepsis is sepsis causing poor organ function or insufficient blood flow. Insufficient blood flow may be evident by low blood pressure, elevated blood lactate or low urine output. Septic shock is low blood pressure due to sepsis that does not improve after reasonable amounts of intravenous fluids are given.

"Post-sepsis syndrome", or "PSS", in the context of the present invention is understood to be a multi-faceted condition that can afflict up to 50% of subjects who recover from a bout of sepsis. The disorder manifests with a number of distinct, overlapping symptoms, including, but not limited to insomnia, vivid hallucinations, panic attacks, pain, particularly in muscles and joints, extreme fatigue, poor concentration and reduced cognitive function. PSS is thought to arise by a variety of mechanisms, with localised pain and neurological defects are thought to arise at least in part due to organ damage and/or failure brought about by the inflammatory response underlying sepsis. Thus, in an embodiment of the invention, the compounds, fatty acids, and compositions disclosed herein in may be used to treat PSS and symptoms associated therewith.

As disclosed herein, "treatment" of PSS encompasses the prevention, ablation or partial reduction of symptoms of PSS. In one embodiment, the compounds, fatty acids, and compositions disclosed herein prevent, ablate or partially reduce all or a number of the following symptoms: insomnia, vivid hallucinations, panic attacks, pain, particularly in muscles and joints, extreme fatigue, poor concentration and reduced cognitive function. In one embodiment, the compounds, fatty acids, and compositions disclosed herein prevent, ablate or partially reduce PSS-associated pain. In one embodiment, PSS-associated pain is chronic neuropathic pain. In another embodiment, the compounds, fatty acids, and compositions disclosed herein prevent, ablate or partially reduce PSS-associated neurological defects.

It is envisaged that the improvement, reduction or elimination of these symptoms is not restricted to patients in the post-sepsis phase. The use of the compounds, fatty acids, and compositions in the methods disclosed herein can also alleviate these symptoms experienced by the patient when administered during an on-going bout of sepsis.

The present inventors have found that compounds of the invention prevent lipopolysaccharide-stimulated secretion of the proinflammatory cytokine IL-6 from freshly isolated peritoneal macrophages. The present inventors have also found that such compounds down-regulate expression of proinflammatory cytokine and chemokine ligand mRNAs in activated macrophages and inhibit the proinflammatory signalling of activated macrophages in vitro. This can be measured using RNAseq analysis of freshly isolated murine peritoneal macrophages stimulated with LPS, in the presence or absence of 10(Z)-hexadecenoic acid. Pathway analysis predicted that the lipid activates peroxisome proliferator-activated receptor signaling. Compounds of the invention are therefore useful in inhibiting the proinflammatory cascade that contributes to the pathology of sepsis.

In a first aspect the invention provides a compound for use in the treatment of sepsis which is an ester of 1,2,3-propanetriol with one or more fatty acids of at least C11, wherein at least one fatty acid has a double bond at the C10-C11 position. The compound will have the general formula:

where $R_1$, $R_2$ and $R_3$ may be the same or different and are either H or a residue of a fatty acid, wherein at least one of $R_1$, $R_2$ and $R_3$ is other than H, and at least one of the fatty acids is at least C11 and has a double bond at the C10-C11 position.

The compound for use in the treatment of sepsis is either a mono-, di- or tri-ester. Preferably the compound for use in the treatment of sepsis is a tri-ester. When the compound for use in the treatment of sepsis is a mono-ester, esterification may occur at the 1- or 2-position. When the compound for use in the treatment of sepsis is a mono-ester preferably esterification occurs at the 1-position. When the compound for use in the treatment of sepsis is a di-ester, esterification may occur at the 1- and 2-positions or at the 1- and 3-positions. When the compound for use in the treatment of sepsis is a di-ester preferably esterification occurs at the 1- and 3-positions.

When the compound for use in the treatment of sepsis is a di-ester the fatty acids may be the same or the fatty acids may be different. Preferably when the compound for use in the treatment of sepsis is a di-ester the fatty acids are the same.

When the compound for use in the treatment of sepsis is a tri-ester the fatty acids may be the same or the fatty acids may be different. Preferably when the compound for use in the treatment of sepsis is a tri-ester the fatty acids are the same.

At least one fatty acid of the compound for use in the treatment of sepsis has a double bond at position C10-C11. The double bond may be cis or trans. In one embodiment, the double bond is cis. In another embodiment, the double bond is trans.

The fatty acid is suitably a $C_{11}$ to $C_{24}$ fatty acid, e.g. $C_{11}$, $C_{12}$, $C_{14}$, $C_{16}$, $C_{18}$, $C_{20}$, $C_{22}$ or $C_{24}$, preferably a $C_{11}$ to $C_{20}$ fatty acid, more preferably a $C_{11}$ to $C_{16}$ fatty acid. In one embodiment at least one fatty acid with a C10-C11 double bond is a $C_{16}$ fatty acid.

The compound for use in the treatment of sepsis is preferably a tri-ester of 1,2,3-propanetriol in which at least one of the fatty acids is 10(Z)-hexadecenoic acid.

In a second aspect the invention provides a fatty acid of at least C11 comprising a double bond at the C10-C11 position for use in the treatment of sepsis. The C10-C11 double bond may be cis or trans. In one embodiment, the double bond is cis. In another embodiment, the double bond is trans. The fatty acid may contain more than one double bond.

The fatty acid may be any $C_{11}$ to $C_{24}$ fatty acid, e.g. $C_{11}$, $C_{12}$, $C_{14}$, $C_{16}$, $C_{18}$, $C_{20}$, $C_{22}$ or $C_{24}$, preferably a $C_{11}$ to $C_{20}$ fatty acid, more preferably a $C_{11}$ to $C_{16}$ fatty acid. In one embodiment the fatty acid with a C10-C11 double bond is a $C_{16}$ fatty acid.

In a particular embodiment the $C_{11}$ to $C_{24}$ fatty acid is 10(Z)-hexadecenoic acid.

In certain embodiments the invention provides a composition comprising the compound of the first aspect or the fatty acid of the second aspect in conjunction with an antibacterial, anti-fungal, or anti-viral molecule that eradicates the infectious agent causing sepsis.

In other embodiments the compound of the first aspect or the fatty acid of the second aspect are for separate, sequential, or simultaneous administration with an antibacterial, anti-fungal, or anti-viral molecule that eradicates an infectious agent causing sepsis, for use in the treatment of sepsis.

The invention also provides the use of the compounds as defined above in the preparation of a medicament for the treatment of sepsis. The inventors have found that the free fatty acid alone is also effective and the invention further provides the use of a $C_{11}$-$C_{24}$ fatty acid having at least one C10-11 double bond in the preparation of a medicament for the treatment of sepsis. The fatty acid is preferably $C_{11}$-$C_{16}$, and more preferably is 10(Z)-hexadecenoic acid.

The compounds, fatty acids and compositions of the invention as defined above are administered by the parenteral route. In particular embodiments, they are administered by subcutaneous, intradermal, subdermal, intraperitoneal, intravenous or intravesicular injection. In preferred embodiments they are administered by intravenous injection.

The compounds of the invention or the free fatty acids as defined above may be used in the preparation of a medicament. The medicament may further comprise standard pharmaceutically acceptable carriers and/or excipients as is routine in the pharmaceutical art. For example, the compound of the invention or the defined free fatty acid may be put into suspension in, for example, a physiological buffer, isotonic saline or water by physical disruption such as ultrasound. Alternatively it may be put into suspension by ultrasound in the presence of a stable carrier protein, for example lipid-free human serum albumin, to which the lipid and/or glycolipid will bind, providing a stable solution.

Alternatively the compounds of the invention or the free fatty acids as defined above may be formulated as slow release pellets following combination with a suitable carrier molecule, for example cholesterol. A suitable carbohydrate that is linked to a lipid or glycolipid may be formulated in the same way as a lipid and/or glycolipid. A suitable carbohydrate not linked to a lipid or glycolipid may be dissolved in, for example, physiological saline or water for injection. The exact nature of a formulation will depend upon several factors including the particular substance to be administered and the desired route of administration. Suitable types of formulation are fully described in Remington's Pharmaceutical Sciences, Mack Publishing Company, Eastern Pennsylvania, 17.sup.th Ed. 1985, the disclosure of which is included herein of its entirety by way of reference.

The pharmaceutical composition comprising compounds of the invention or the free fatty acids as defined above may also contain further ingredients such as adjuvants, preservatives, stabilisers etc. It may further comprise other therapeutic agents. It may be supplied in sterile and pyrogen-free form, for example as an injectable liquid; in sterile freeze-dried form which is reconstituted prior to use; or as sterile slow-release pellets. The pharmaceutical composition may be supplied as an isotonic liquid. It may be supplied in unit dosage form.

In a third aspect the invention provides a method of treating sepsis comprising administration of a compound which is an ester of 1,2,3-propanetriol and one or more fatty acids of at least C11, wherein at least one fatty acid has at least one double bond, at the C10-C11 position, to a patient in need of such treatment.

The compound can be a mono-, di- or tri-ester, but preferably it is a tri-ester. When the compound is a mono-ester, esterification may occur at the 1- or 2-position, but preferably esterification occurs at the 1-position. When the compound is a di-ester, esterification may occur at the 1- and 2-positions or at the 1- and 3-positions, but preferably esterification occurs at the 1- and 3-positions.

When the compound is a di-ester or a tri-ester the fatty acids may be the same or the fatty acids may be different, but preferably the fatty acids are the same.

At least one fatty acid of the compound has at least one double bond, at position C10-C11. The double bond may be cis or trans. In one embodiment, the double bond is cis. In another embodiment, the double bond is trans. The fatty acid may comprise a single double bond, at the C10-C11 position.

The fatty acid is suitably a $C_{11}$ to $C_{24}$ fatty acid, e.g. $C_{11}$, $C_{12}$, $C_{14}$, $C_{16}$, $C_{18}$, $C_{20}$, $C_{22}$ or $C_{24}$, preferably a $C_{11}$ to $C_{20}$ fatty acid, more preferably a $C_{11}$ to $C_{16}$ fatty acid. In one embodiment the at least one fatty acid with a C10-C11 double bond is a $C_{16}$ fatty acid.

The compound is preferably a tri-ester of 1,2,3-propanetriol in which at least one of the fatty acids is 10(Z)-hexadecenoic acid.

In preferred embodiments the method further comprises the separate, sequential, or simultaneous administration of an antibacterial, anti-fungal, or anti-viral molecule known to eradicate the infective agent causing sepsis.

In a fourth aspect the invention provides a method of treating sepsis comprising administration of a fatty acid of at least C11 comprising a double bond between C10 and C11 to a patient in need of such treatment.

The fatty acid may be any $C_{11}$ to $C_{24}$ fatty acid, e.g. $C_{11}$, $C_{12}$, $C_{14}$, $C_{16}$, $C_{18}$, $C_{20}$, $C_{22}$ or $C_{24}$, preferably a $C_{11}$ to $C_{20}$ fatty acid, more preferably a $C_{11}$ to $C_{16}$ fatty acid. In one embodiment the fatty acid with a C10-C11 double bond is a $C_{16}$ fatty acid.

In a particular embodiment the fatty acid is 10(Z)-hexadecenoic acid.

In preferred embodiments the method further comprises the separate, sequential, or simultaneous administration of an antibacterial, anti-fungal, or anti-viral molecule known to eradicate the infectious agent causing sepsis to a patient in need of such treatment.

In the methods of the invention the compounds, fatty acids and compositions as defined above are administered by the parenteral route. In particular embodiments of the method they are administered by subcutaneous, intradermal, subdermal, intraperitoneal, intravenous or intravesicular injection. In preferred embodiments they are administered by intravenous injection.

In another embodiment, the compounds, fatty acids and compositions as defined above are administered via the enteral route, preferably by intratracheal administration. In one embodiment, the compound, fatty acids and compositions are administered via an inhaler.

A therapeutically effective amount of the compound of the invention or the free fatty acids as defined above is administered to a patient. The dose may be determined according to various parameters, especially according to the substance used; the age, weight and condition of the patient to be treated; the route of administration; and the required regimen. A physician will be able to determine the required route of administration and dosage for any particular patient. Multiple doses may be given. A typical individual dose is from about 0.005 to 1.0 mg/kg, preferably from about 0.01 to 0.5 mg/kg, more preferably from about 0.03 to 0.3 mg/kg, according to the activity of the specific lipid preparation, the age, weight and condition of the subject to be treated, the type and severity of the condition and the frequency and route of administration.

For the purposes of the present invention, the lipids derived from *Mycobacteria* can be extracted by a number of alternative processes well known in the art. For example, cells containing the lipid of interest can be incubated with an extraction media that promotes dissolution of the lipids from the other components of the cell. Generally, suitable extraction media will comprise a mixture of organic and aqueous solvents that when incubated for sufficient time separate into immiscible layers based on a gradation of hydrophobicity. After a period of incubation of the cells in the extraction media under conditions that favour the dissolution of cells, the extraction media can be allowed to settle into the individual immiscible layers (or aqueous phases), each of which will contain a different cellular faction or, more specifically, a different lipid fraction, with the most apolar lipids existing in the most hydrophobic component of the extraction media. The different aqueous phases can then be individually aspirated to separate the various lipid fractions. Further separation of the lipids within each layer is possible; by rehydrating the dried lipid films in a secondary extraction media. One particular non-limiting example of an extraction media suitable for the primary extraction of lipids comprises a mixture of petroleum ether, methanol and 0.3% aqueous sodium chloride solution. Other suitable media for primary and secondary extractions will be well known to the skilled artisan. Alternatively, or in combination with the above, lipids may be extracted or purified from the milieu using gradient liquid chromatography in a mixture of suitable organic solvents, such as increasing amounts of methanol in chloroform, or by thin-film chromatography. The identity of the extracted lipid can be determined using any number of analytical techniques, including, but not limited to, mass spectrometry, infrared spectroscopy and 1D-NMR.

Figure 6:
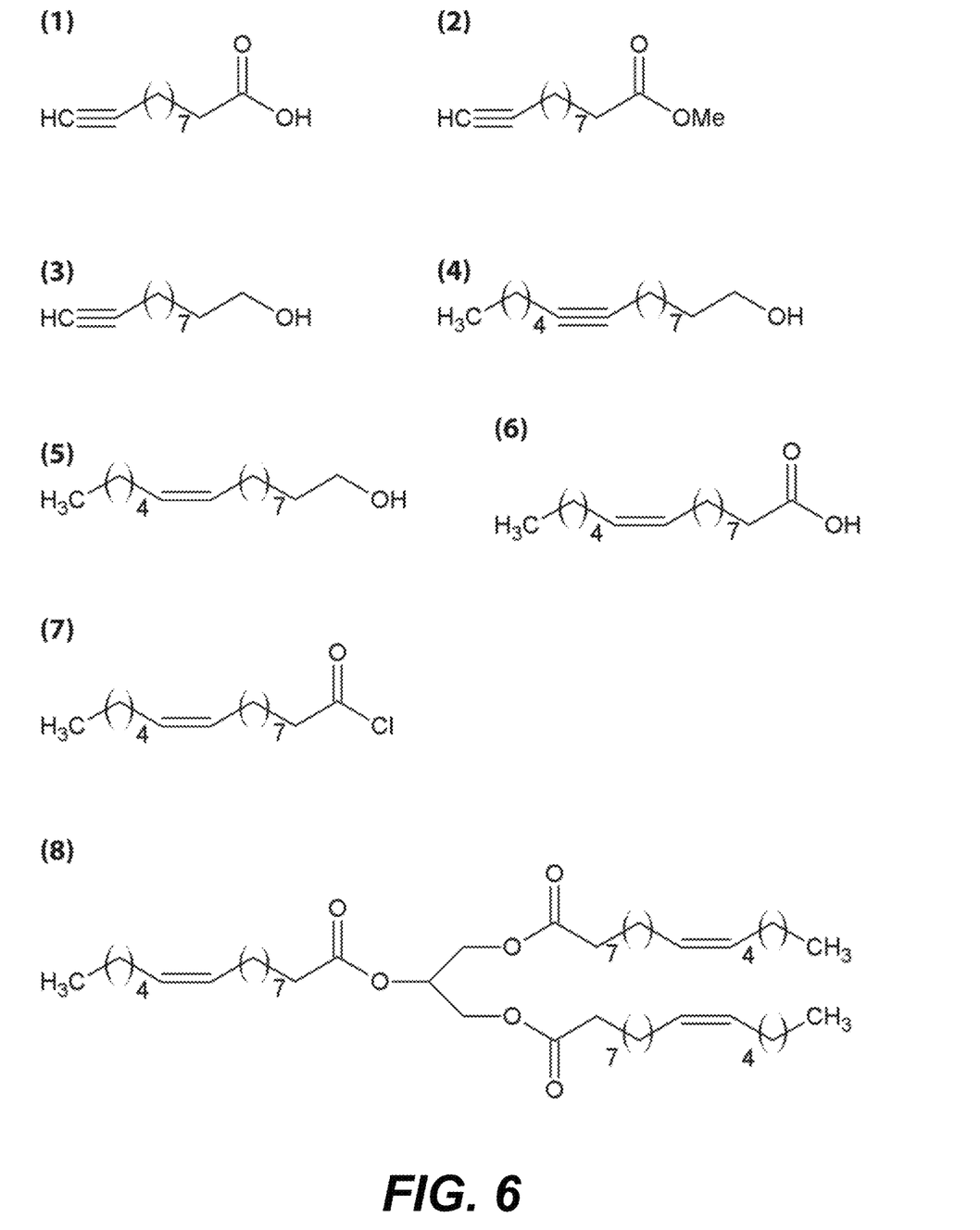
FIG. 6 shows chemical structures associated with the synthesis of the triacylglycerol.

Compounds for use in the treatment of sepsis of the invention may be synthesised by a process which is defined in the examples accompanied by a schematic illustration in FIG. 6. More generally, however, the skilled person would appreciate that the starting materials of the chemical synthesis could be modified in order to control or modify the length of the fatty acid chain. The skilled person would also acknowledge that the reaction times, conditions, temperature, pressure, reactant concentrations, and yields resulting from each step of the synthesis may vary according to the starting materials used. Additional steps could also be incorporated in order to introduce additional double bonds into the fatty acid molecule. The optimisation of each step within the synthetic route when using different starting materials is well within the purview of the skilled person. Fundamentally, modifying the starting materials simply requires trial and error in order to achieve effective synthesis of the fatty acid molecule, or triacylglycerol esters thereof, of varying chain length that comprises at least a double bond at positions C10 to C11.

Throughout the present specification and the accompanying claims the words "comprise" and "include" and variations such as "comprises", "comprising", "includes" and "including" are to be interpreted inclusively. That is, these words are intended to convey the possible inclusion of other elements or integers not specifically recited, where the context allows.

EXAMPLES

The fractionation of *M. vaccae* NCTC 11659 with a number of solvents resulted in the isolation of several lipid fractions with different characteristics. Preliminary work identified lipids present in the aqueous methanol fraction, such as phospholipids, polar and neutral glycolipids and glycosylphosphatidylinositols, but not those in the petrol fraction, such as phthiocerols, dimicocerosates and mycolic acids, to be of considerable interest.

Pretreatment with an Aqueous Methanol Extraction of *M. vaccae* Reduces Allergic Pulmonary Inflammation Upon further fractionation of the aqueous methanol fraction, the phospholipid, polar glycolipid and glycosylphosphatidylinositol components (fraction 147) were separated from the neutral glycolipid components (fraction 148).

Figure 7:
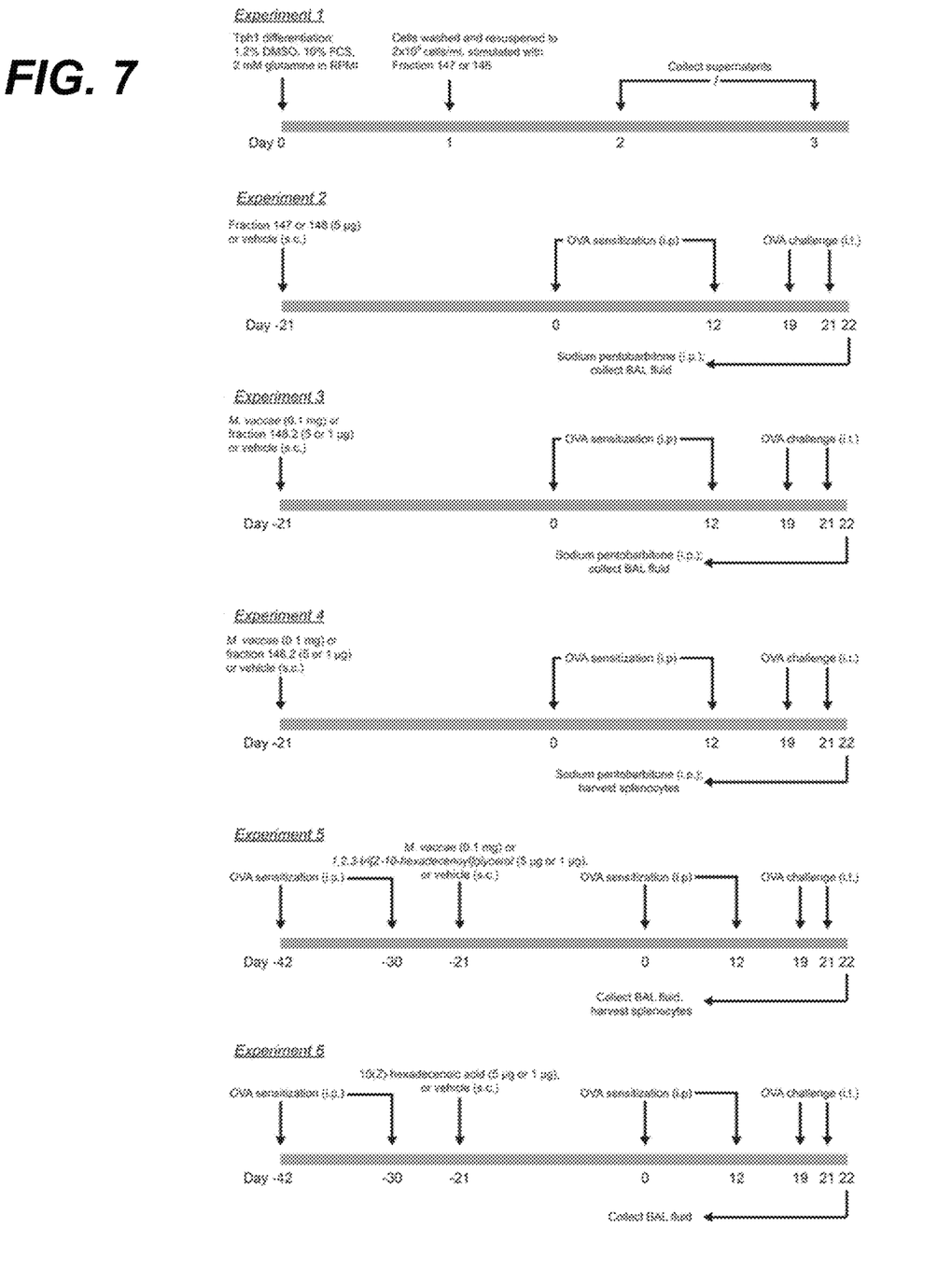
FIG. 7 shows a diagrammatic illustration of six experimental designs, in which the following abbreviations are used: BAL, bronchoalveolar lavage; i.p., intraperitoneal; i.t., intratracheal; OVA, chicken egg ovalbumin; s.c., subcutaneous; DMEM, Dulbecco's Modified Eagle Medium; LPS, lipopolysaccharide; FBS, fetal bovine serum; DPBS, Dulbecco's Phosphate-Buffered Saline.

In Experiment 1, the immunomodulatory properties of the two fractions were assessed in vitro using Thp1 cells, a human monocytic cell line, exposed overnight to these preparations (for experimental timeline, see FIG. 7, Experiment 1). It was found that Thp1 cells stimulated with fraction 147 preferentially produce IL-12p40. In contrast when stimulated with fraction 148 they showed reduced IL-12p40 secretion and an increase in IL-10 levels.

In Experiment 2 mice were treated, subsequently rendered allergic by immunization with ovalbumin and alum on Days 0 and 12, with either a heat-killed preparation of *M. vaccae* (NCTC 11659; 0.1 mg, s.c.) or fraction 147 and 148, (5 µg; s.c.) on Day −21 and determined their respective potential in limiting allergic pulmonary inflammation, measured on Day 22 following intratracheal (i.t.) ovalbumin challenge on Days 19 and 21 (for experimental timeline, see FIG. 7, Experiment 2).

Pulmonary allergic inflammation is associated with a large influx of cells, particularly eosinophils, in the airway. We found that mice treated with either a heat-killed preparation of *M. vaccae* NCTC 11659 or fraction 148 showed a significant reduction in both the total cellular infiltrate and in the number of eosinophils recovered in the bronchoalveolar lavage (BAL) fluid (Table 1).

The decrease in eosinophils was not associated with an increase in other inflammatory cells. In fact, macrophages ($p<0.05$) were also reduced at the site of inflammation, while there were no effects on numbers of neutrophils (Table 1).

This reduction in disease severity was not observed in allergic mice treated with fraction 147. These results suggest that, not only do fractions 147 and 148 have different immunological properties, but also that fraction 148 prevents pulmonary allergic inflammation in a mouse model.

TABLE 1

Characterization of the cellular infiltrate in the lungs of allergic mice challenged intratracheally with ovalbumin in Experiment 2.

| | | Cell × $10^5$/ml | | |
|---|---|---|---|---|
| | Vehicle | *M. vaccae* NCTC 11659 | Fraction 147 | Fraction 148 |
| Total cellular infiltrate | 2.14 ± 0.2 | 0.65 ± 0.1* | 1.73 ± 0.36 | 0.55 ± 0.1* |
| Eosinophils | 0.41 ± 0.1 | 0.17 ± 0.01* | 0.49 ± 0.2 | 0.12 ± 0.01* |
| Neutrophils | 0.12 ± 0.04 | 0.03 ± 0.02 | 0.07 ± 0.02 | 0.02 ± 0.02 |
| Macrophages | 1.57 ± 0.1 | 0.45 ± 0.1* | 1.15 ± 0.2 | 0.42 ± 0.1* |

*denotes $p < 0.05$ in Bonferroni-corrected ANOVA compared with vehicle-treated, ovalbumin-challenged mice. These results are representative of at least two separate experiments (n = 8 per group).

Specific Fractions of the Mycobacterial Extract are Anti-Inflammatory In Vitro

Fraction 148 was further fractionated by column chromatography using a chloroform-methanol gradient. Based on previous results we screened seven subfractions of fraction 148 using Thp1 cells for a cytokine profile associated with low IL-12p40 and increased IL-10 levels. Following these criteria, three subfractions were identified as having interesting features, and fraction 148.2 was used in further experiments.

Figure 1A:
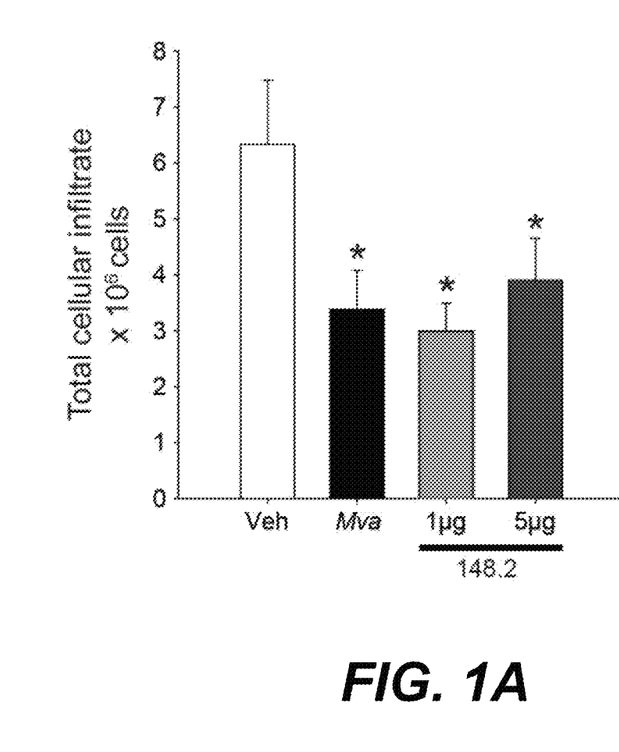
FIGS. 1A and 1B show data obtained from Experiment 2 showing that *M. vaccae* and *M. vaccae* fraction 148.2 reduce bronchopulmonary inflammation. Treatment with lipid fraction 148.2 of *M. vaccae* reduced the severity of pulmonary allergic inflammation.
Figure 1B:
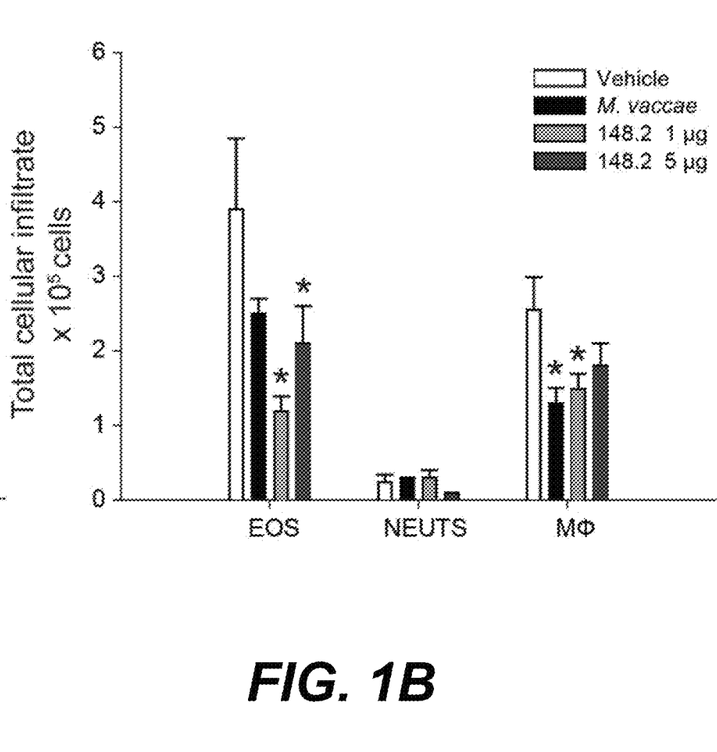

In Experiment 3 (for experimental timeline, see FIG. 7, Experiment 3) it was demonstrated that mice treated with either *M. vaccae* NCTC 11659 (0.1 mg, s.c.) or two different doses of fraction 148.2 (5 µg and 1 µg, s.c.) showed a significant reduction in both the total cellular infiltrate and/or the number of eosinophils or macrophages recovered in the BAL fluid (FIGS. 1A and 1B).

Additionally, in Experiment 4 (for experimental timeline, see FIG. 7, Experiment 4), the effects of *M. vaccae* NCTC 11659 (0.1 mg, s.c.) and fraction 148.2 (5 µg or 1 µg, s.c.) on IL-10 secretion from splenocytes stimulated with allergen ex vivo were studied. Splenocytes from mice treated with *M. vaccae* NCTC 11659 and mice treated with fraction 148.2 produced increased levels of IL-10 following in vitro allergen (ovalbumin) stimulation (*M. vaccae* NCTC 11659, 234±47 pg/ml; 1 µg fraction 148.2, 227±20 pg/ml; 5 µg fraction 148.2, 291±16 pg/ml), compared to levels from splenocytes of mice treated with vehicle alone (179±37 pg/ml). These results suggest that components of fraction 148.2 maintain the induction, in vitro, of a cytokine profile associated with prevention of pulmonary allergic inflammation in a mouse model.

The Anti-Inflammatory Component of the Fraction is a Triglyceride

By performing a series of analytic chemistry experiments including high resolution mass spectrometry (HRMS), 1-dimensional (1D) ($^1$H and $^{13}$C) and two-dimensional (2D) (correlation spectroscopy (COSY) and $^1$H/$^{13}$C heteronuclear multiple bond correlation (HMBC)) nuclear magnetic resonance (NMR) spectroscopy, and gas chromatography-mass spectrometry (GC-MS) analyses, it was concluded that fraction 148.2 is a triacylglycerol. From the $^1$H signals a glycerol backbone at 4.20 ppm (4H) and 5.25 ppm (1H) was identified. A complex signal at 5.32 ppm (3.3H, CH=CH), 2.3 ppm (6H, CO—CH$_2$), 2.0 ppm (8H, CH$_2$CH=CHCH$_2$) and 1.6 ppm (8H, CO—CH$_2$CH$_2$) was also obtained. Electrospray mass spectrometry analysis of the triacylglycerol yielded the sodiated molecular ion at a mass-to-charge ratio (m/z) 823. Further analysis of fatty acid characteristics revealed that fraction 148.2 contained predominantly C16 and C18:1 and a smaller proportion of C18 and C16:1. The position of the double bond was determined. The connectivity pattern was consistent with a cis double bond for C18:1 at position 9,10 and, surprisingly, at position 10,11 for C16:1. The latter is a rather unusual lipid and appears to be restricted to *Mycobacteria* spp. (see compound (8) in FIG. 6), although lactobacilli have been shown to have capacity to synthesize, from γ-linolenic acid, C18:1 fatty acids with a double bond at position 10,11 (Ogawa, J. et al. (2005) J. Biosci. Bioeng. 100:355-364).

The Triglyceride, 1,2,3-Tri[Z-10-Hexadecenoyl]Glycerol, has Therapeutic Potential in a Mouse Model of Pulmonary Allergic Inflammation Whether treatment with this triacylglycerol alone retains the therapeutic activity initially observed for treatment with whole *M. vaccae* NCTC 11659 was investigated in Experiment 5. To this end, the C16:1 triacylglycerol with a double bond at position 10,11 of each acyl chain (hereafter referred to as 1,2,3-tri[Z-10-hexadecenoyl]glycerol) was synthesized and its therapeutic potential in a mouse model of allergic pulmonary inflammation was determined (for experimental timeline, see FIG. 7, Experiment 5).

Figure 2:
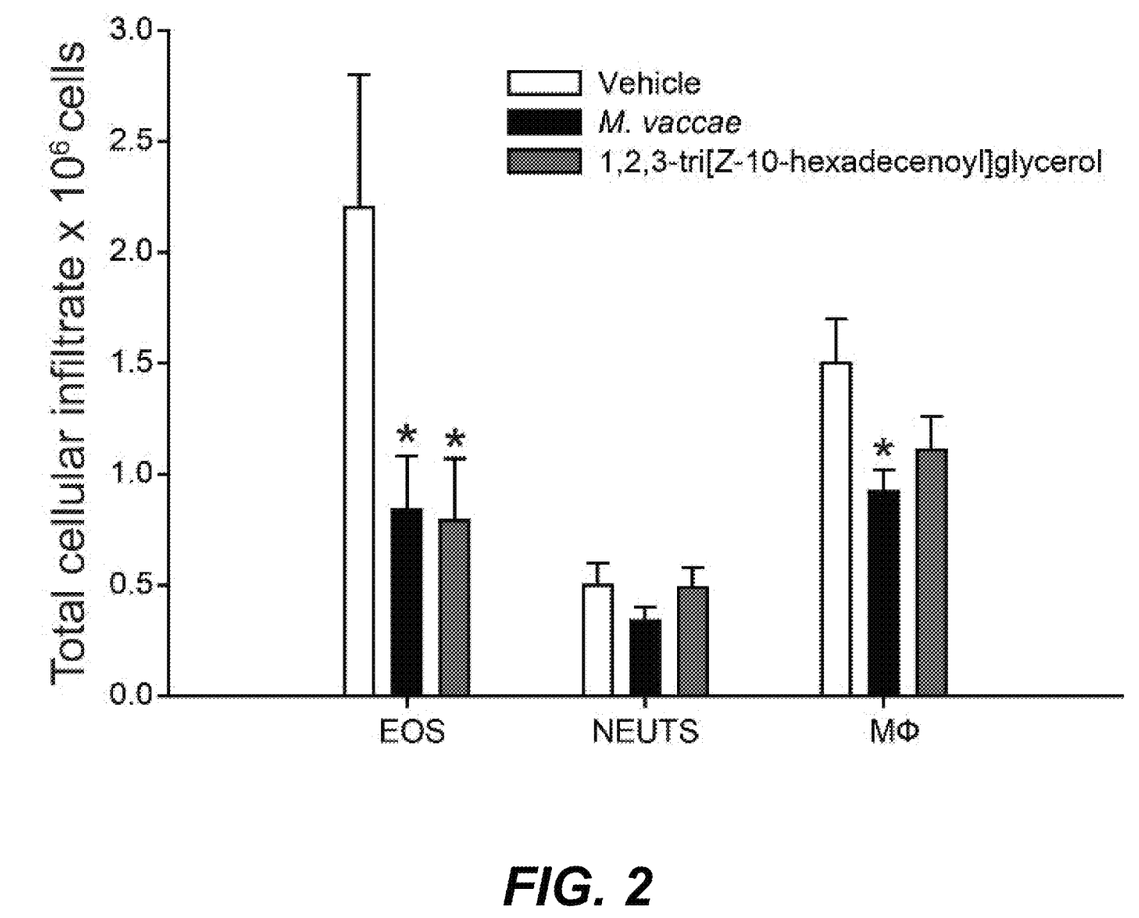

It was found that mice treated with either *M. vaccae* NCTC 11659 (0.1 mg, s.c.) or 1,2,3-tri[Z-10-hexadecenoyl] glycerol (5 µg, s.c.) showed a reduction in both the total cellular infiltrate and in the number of eosinophils recovered in the BAL fluid (FIG. 2). Once again the reduction in eosinophilia was not accompanied by an increase in Type1-mediated inflammation as the numbers of macrophages were not increased. The reduction in the number of eosinophils was comparable to that seen following treatment with heat-killed whole cell *M. vaccae* NCTC 11659 (FIG. 2).

Figure 3A:
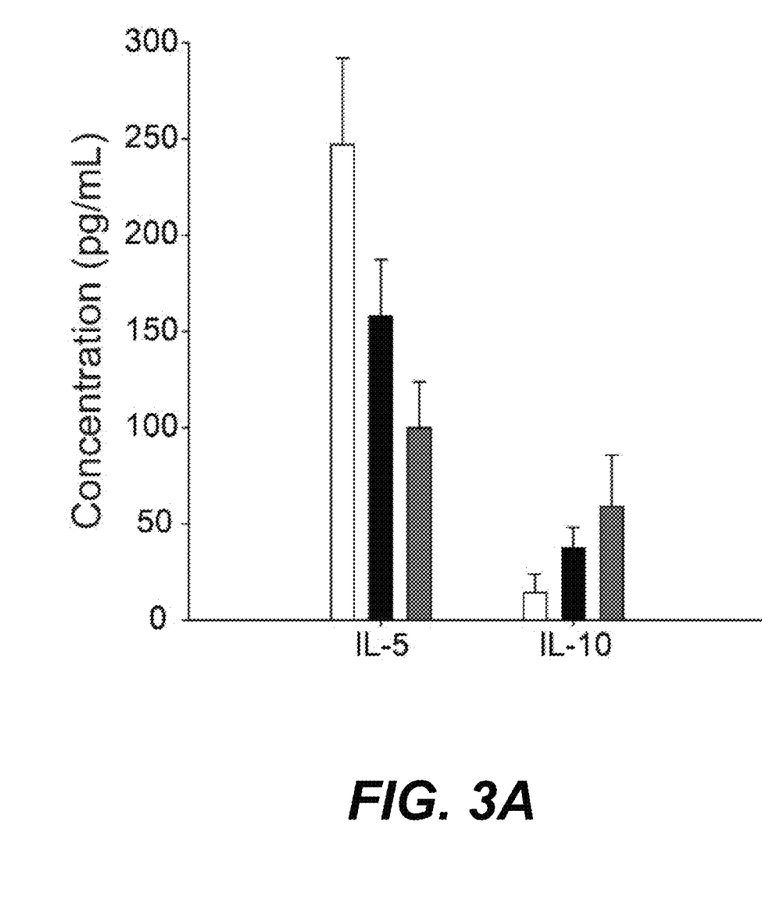
FIGS. 3A and 3B show data from Experiment 3 showing that the synthetic triglyceride, 1,2,3-tri[Z-10-hexadecenoyl] glycerol, has an anti-inflammatory effect on immune cells recovered by bronchoalveolar lavage (BAL) fluid and splenocytes. Treatment with a synthetic lipid originally obtained from *M. vaccae* altered the cytokine profile of allergic mice.
Figure 3B:
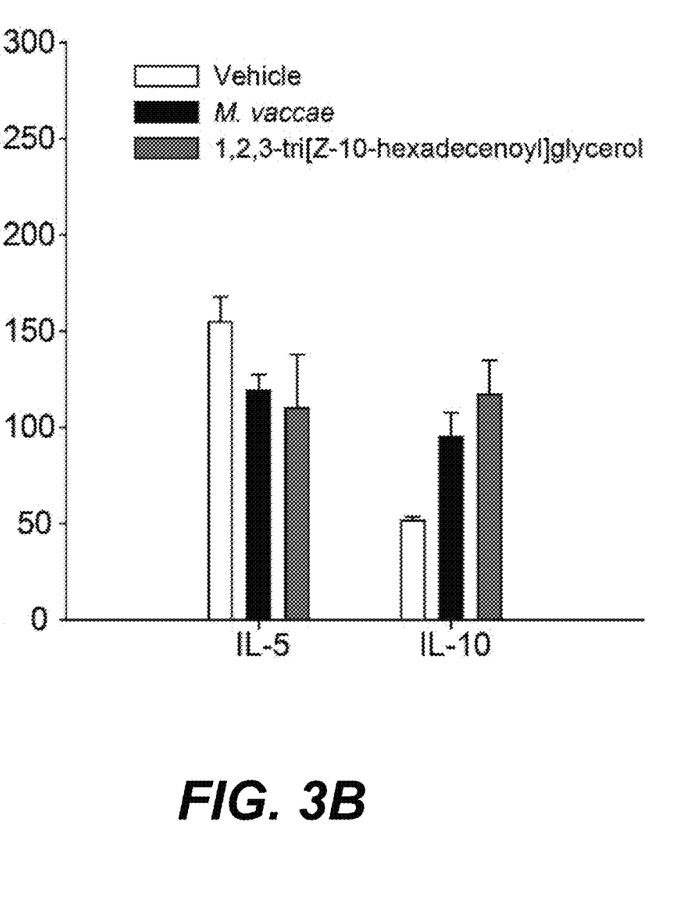

Additionally, a decrease in IL-5 concentrations and an increase in IL-10 concentrations in the BAL fluid of mice treated with 1,2,3-tri[Z-10-hexadecenoyl]glycerol compared to those measured in the BAL fluid of mice treated with vehicle were observed (FIG. 3A). Levels of IFN-γ were below detection in the BAL fluid of allergic mice regardless of treatment. Cytokine levels were measured in the supernatant of in vitro splenocyte culture following allergen stimulation. An increase in IL-10 and a decrease in IL-5 levels in the supernatant of splenocytes of mice treated with 1,2,3-tri[Z-10-hexadecenoyl]glycerol were found compared to those in the supernatant of splenocytes of mice treated with buffer (FIG. 3B). These results are the first to show therapeutic activity of a synthetic lipid, 1,2,3-tri[Z-10-hexadecenoyl]glycerol, of *M. vaccae* NCTC 11659 in a mouse model of pulmonary allergic inflammation.

The free fatty acid, 10(Z)-hexadecenoic acid, was also synthesized in order to determine if the triglyceride structure was necessary for therapeutic function of 1,2,3-tri[Z-10-hexadecenoyl]glycerol. This was tested in Experiment 6 (for experimental timeline, see FIG. 7, Experiment 6).

In the mouse model of allergic pulmonary inflammation, the free fatty acid provided a significant reduction of both eosinophilia and total cellular infiltrate. Furthermore, 10(Z)-hexadecenoic acid treatment did not induce increases in macrophages or neutrophils. As was seen for 1,2,3-tri[Z-10-hexadecenoyl]glycerol, a decrease in IL-5 concentrations and an increase in IL-10 concentrations in the BAL fluid of 10(Z)-hexadecenoic acid-treated mice was observed. From these results, it was concluded the anti-inflammatory effects of 1,2,3-tri[Z-10-hexadecenoyl]glycerol are not due to the molecule's multivalency, but rather they are due to its acyl chains.

10(Z)-Hexadecenoic Acid Prevents LPS-Induced Secretion of IL-6 in Macrophages

Experiment 7 was carried out to resolve if 10(Z)-hexadecenoic acid has a direct effect on immune cells. Macrophages were selected for this study on account of their ubiquity and diverse role in immune processes. To simulate inflammation, freshly isolated mouse peritoneal macrophages were challenged with lipopolysaccharide (LPS; 1 µg/mL) ex vivo.

Figure 4A:
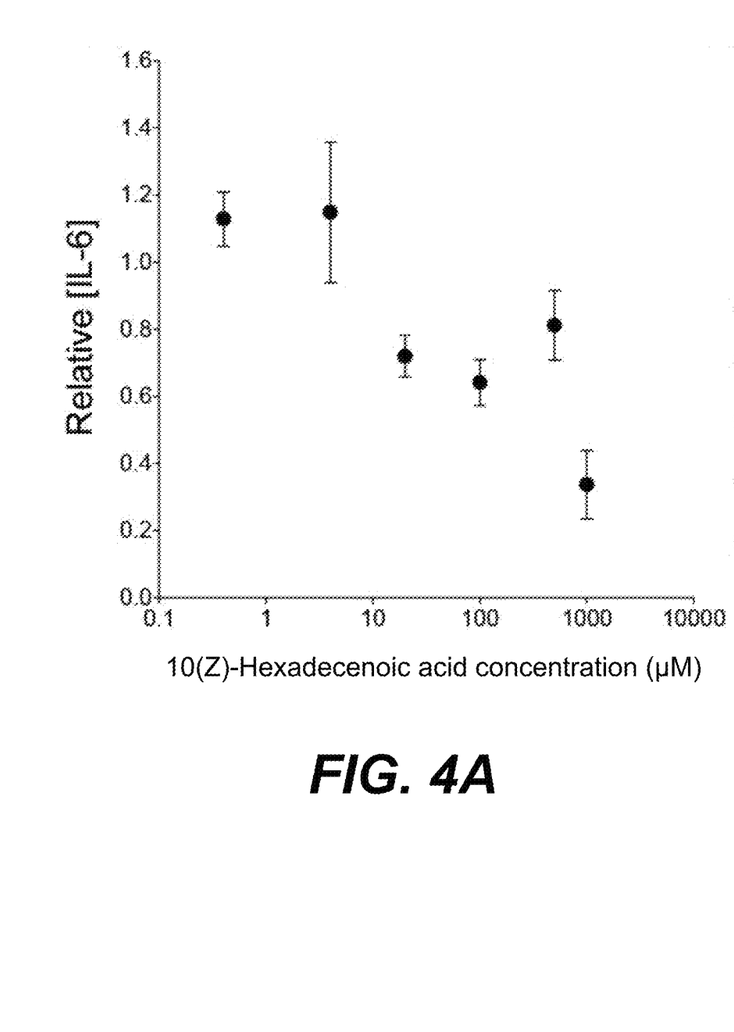
FIGS. 4A-4D show anti-inflammatory effects of 10(Z)-hexadecenoic acid in freshly-isolated murine peritoneal macrophages. Freshly isolated murine peritoneal macrophages were incubated for 1 h with 10(Z)-hexadecenoic acid (0.4 µM, 4 µM, 20 µM, 100 µM, 500 µM, 1000 µM), then challenged with 1 µg/mL lipopolysaccharide (LPS). Cell supernatants were collected at 6 h (FIG. 4A), 12 h (FIG. 4B), and 24 h (FIG. 4C) after LPS challenge. Interleukin (IL)-6 concentrations in the supernatant were determined using ELISA and reported relative to media-only controls (n=6 replicates, with each replicate using different freshly isolated peritoneal macrophages; each sample was run in duplicate).
Figure 4B:
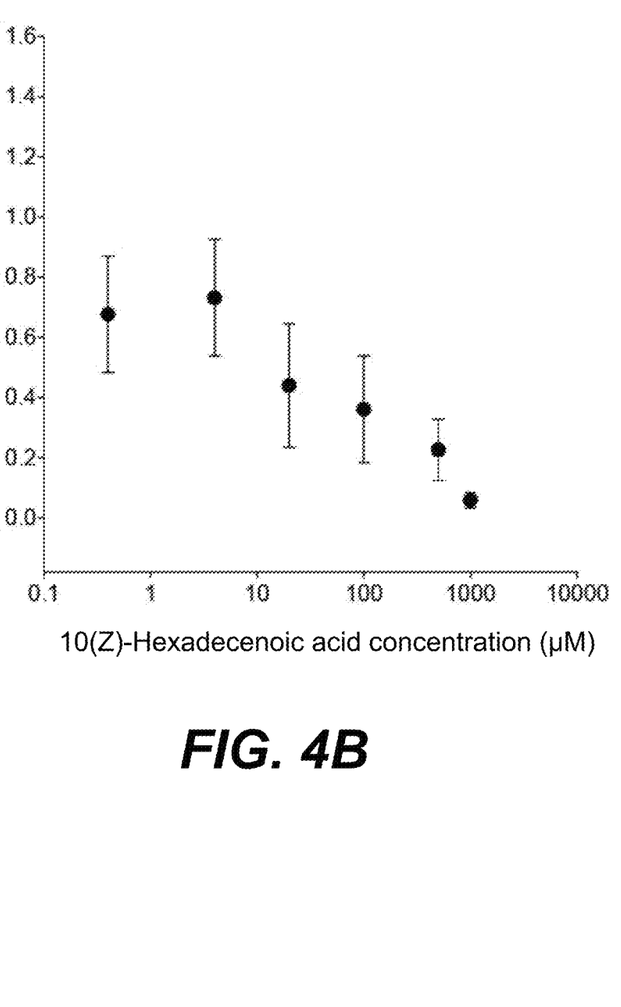
Figure 4C:
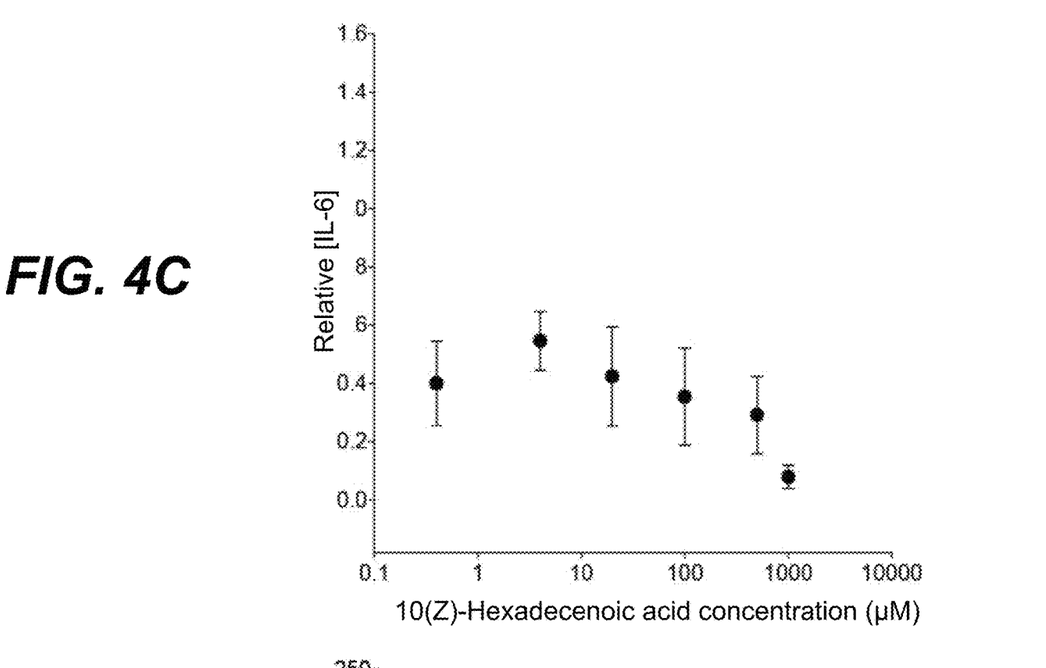
Figure 4D:
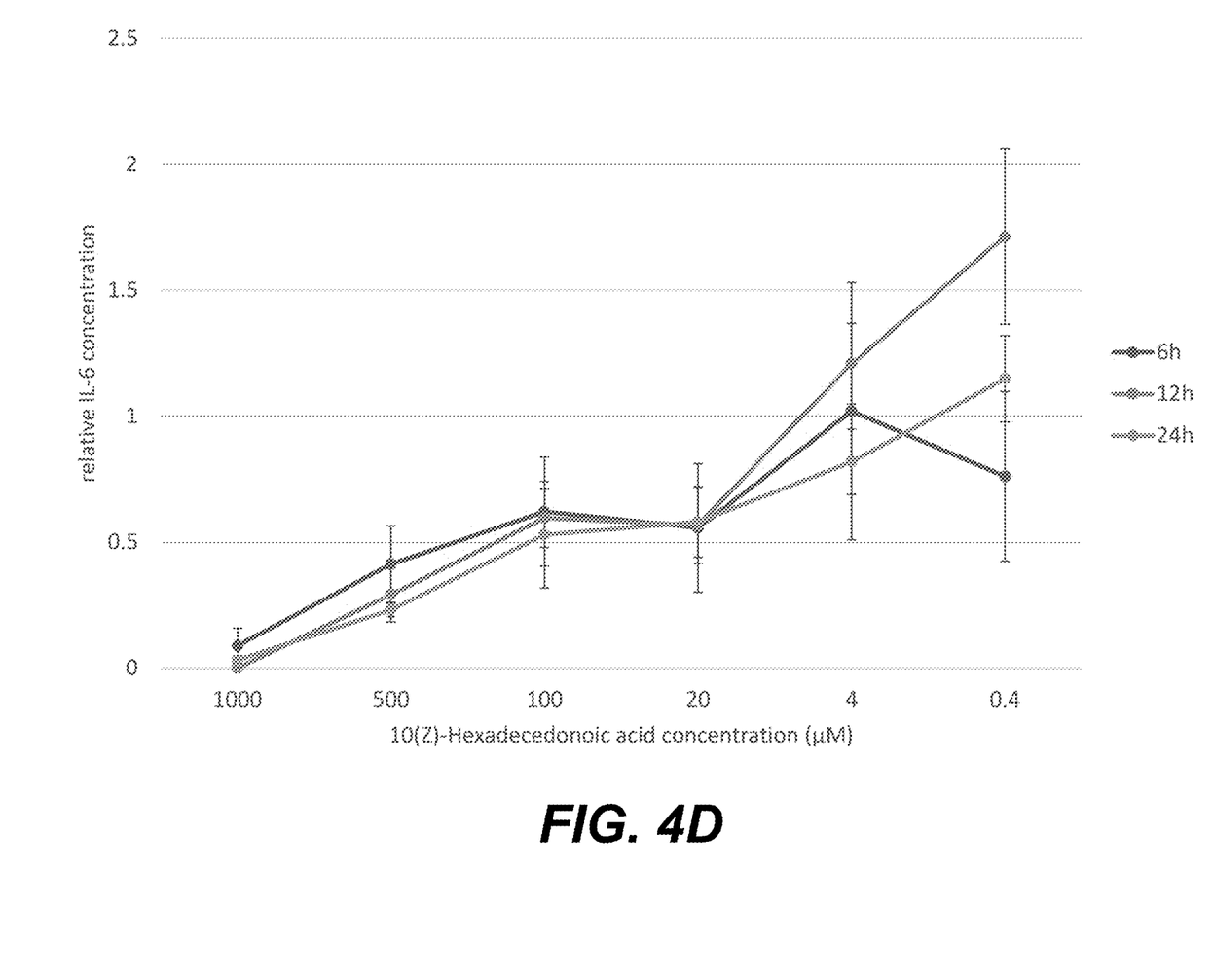

Macrophages that were cultured in the presence of 10(Z)-hexadecenoic acid for 1 h prior to LPS treatment secreted less IL-6 compared to macrophages cultured with media alone (FIGS. 4A-4C). This difference was observable as early as 6 h after LPS challenge, and was sustained for at least 24 h. The effect also appeared to be concentration and time dependent. The lowest concentration of 0.4 µM was ineffective at 6 h, but reduced IL-6 secretion to 40% of control levels at 24 h. This time and concentration dependence may indicate that a receptor-mediated transcriptional change is occurring. In contrast to the effects of 10(Z)-hexadecenoic acid on LPS-induced IL-6 secretion, it had no effect of IL-6 secretion by itself (FIG. 4D). A transcriptional change was confirmed by measurement of pro-inflammatory cytokine and chemokine ligand mRNA levels in macrophages pre-treated with 10(Z)-hexadecenoic acid for 1 h prior to LPS treatment (Table 2).

Figure 5:
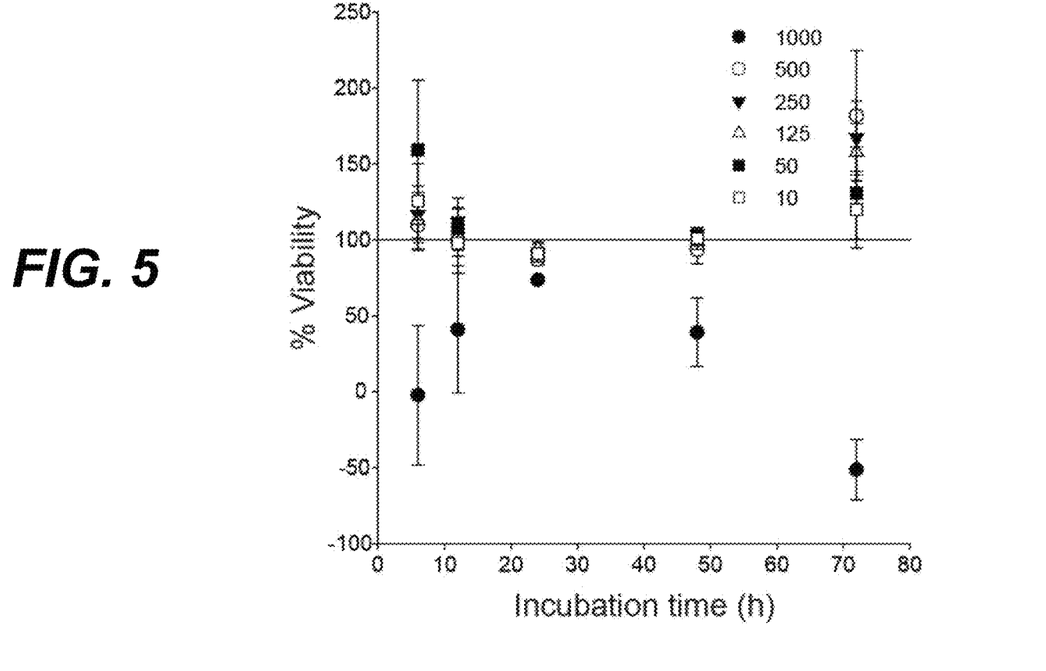

Cell viability was measured to dispel the possibility that senescence or cell death was contributing to reduced IL-6 secretion. Using a high concentration (1 mM) of 10(Z)-hexadecenoic acid, less than 40% of macrophages were viable at most time points. However, macrophages cultured with all other concentrations of 10(Z)-hexadecenoic acid were as viable as or more viable than media controls (FIG. 5).

TABLE 2

Proinflammatory cytokine and chemokine ligand mRNAs downregulated by preincubation of freshly isolated murine peritoneal macrophages with a synthetic, M. vaccae-derived fatty acid, 10(Z)-hexadecenoic acid, prior to stimulation with lipopolysaccharide.

| Gene | Mean #Reads LPS (n =3) | Mean #Reads s148.2 + LPS (n = 3) | Effect | Fold-change | Log2 Fold-change | p value | Adjusted p value |
|---|---|---|---|---|---|---|---|
| Il6 | 1302 | 305 | ↓ | 0.23 | −2.09 | 4.19E−23 | 4.37E−19 |
| Il1b | 15,957 | 5349 | ↓ | 0.34 | −2.16 | 4.03E−15 | 6.48E−12 |
| Ccl7 | 1182 | 441 | ↓ | 0.37 | −1.42 | 3.37E−12 | 3.35E−9 |
| Ccl2 | 5656 | 2234 | ↓ | 0.39 | −1.34 | 5.18E−12 | 4.91E−9 |
| Il12a | 714 | 268 | ↓ | 0.37 | −1.42 | 5.70E−11 | 4.57E−8 |
| Ccl22 | 327 | 117 | ↓ | 0.36 | −1.48 | 5.15E−10 | 3.26E−7 |
| Ccl6 | 810 | 368 | ↓ | 0.45 | −1.14 | 5.31E−8 | 2.36E−5 |
| Tnf | 2098 | 1023 | ↓ | 0.49 | −1.04 | 2.95E−7 | 1.04E−4 |
| Ccl17 | 24 | 3 | ↓ | 0.12 | −3.08 | 3.97E−7 | 1.34E−4 |
| Il1a | 16533 | 8500 | ↓ | 0.51 | −0.96 | 1.02E−6 | 3.19E−4 |
| Ccl4 | 603 | 305 | ↓ | 0.51 | −0.98 | 3.75E−6 | 1.02E−3 |
| Il11 | 26 | 5 | ↓ | 0.20 | −2.35 | 1.59E−5 | 3.7E−3 |
| Cxcl2[1] | 4726 | 2680 | ↓ | 0.57 | −0.82 | 3.01E−5 | 6.4E−3 |
| Ccl3 | 6693 | 4067 | ↓ | 0.61 | −0.72 | 1.99E−4 | 2.9E−2 |

[1]Cxcl2 is a functional homologue of human IL-8

Experimental Materials and Methods

Animals

For studies involving isolation of bacterially-derived small molecules, and in vivo studies, adult female BALB/c mice, 6-8 weeks old, (Harlan, Abingdon, UK) were housed under standard conditions with food and water available ad libitum. For studies involving ex vivo studies of freshly isolated peritoneal macrophages, adult male BALB/c mice (BALB/cAnHsd; Cat. No. 047; Harlan, Indianapolis, Ind., USA), 6-8 weeks old, were used and housed under standard conditions with food and water available ad libitum.

For studies involving isolation of bacterially-derived small molecules, and in vivo studies, all experimental protocols complied with the Home Office 1986 Animals Scientific Act. For studies involving ex vivo studies of freshly isolated peritoneal macrophages, all experimental protocols were consistent with the National Institutes of Health Guide for the Care and Use of Laboratory Animals, Eighth Edition (The National Academies Press, 2011) and the Institutional Animal Care and Use Committee at the University of Colorado Boulder approved all procedures. All possible efforts were made to minimize the number of animals used and their suffering.

Mycobacterium vaccae

Isolation of bacterially-derived small molecules from M. vaccae was conducted using sterile paste derived from freshly grown stocks. For in vivo studies, sterile vials of heat-killed whole cell M. vaccae suspension (10 mg/ml; strain NCTC 11659) were supplied by SR Pharma (London, UK). For studies involving ex vivo studies of freshly isolated peritoneal macrophages, the same material was provided by BioElpida (Lyon, France; batch ENG #1).

Isolation of Lipids

Wet cells (200 g of paste of sterile heat-killed whole cell M. vaccae) were extracted using 440 mL of petroleum ether, 400 mL of methanol, and 40 mL 0.3% aqueous sodium chloride overnight with gentle agitation. The mixture was then left to stand and the upper organic petroleum-ether supernatant fraction was separated by careful aspiration. The lower aqueous phase was extracted again using petroleum ether (400 mL) as described above. The petroleum-ether extracts were combined and dried to yield the apolar lipids. The lower aqueous phase was then extracted using chloroform/methanol/water (90:100:30; 520 mL) with gentle agitation, overnight. The resulting lipid extract was separated by vacuum filtration and the residual biomass extracted using chloroform/methanol/water (50:100:40; 170 mL) overnight with gentle agitation twice. The three polar lipid extractions were combined and chloroform (290 mL) and 0.3% aqueous sodium chloride (290 mL) was added. The entire mixture was briefly shaken, allowed to settle and the upper phase was carefully removed and discarded. The lower organic layer was dried to yield the polar lipids. The polar lipids were resuspended in a minimum volume of chloroform (20 mL) and added to chilled acetone (1.5 L) and left at 4° C., overnight. The resulting precipitate (lipid fraction 147) was separated by centrifugation from the acetone soluble lipids (220 mg) designated lipid fraction 148. Fraction 148 was further fractionated using column chromatography using increasing amounts of methanol in chloroform to afford seven lipidic fractions. These were screened for their immunomodulatory potential as described below. While a number of fractions were deemed interesting, fraction 148.2 (82 mg) was further analyzed. The resulting fraction was deemed pure by thin-layer chromatography (TLC) using chloroform as an eluant following charring with a heat gun after spraying with 5% ethanolicmolybdo-phosphoric acid. Through a combination of high resolution mass spectrometry (HRMS), 1-dimensional (1D) ($^1$H and$^{13}$C), and two-dimensional (2D) (correlation spectroscopy (COSY) and $^1$H/$^{13}$C heteronuclear multiple bond correlation (HMBC)) nuclear magnetic resonance (NMR) spectroscopy, and gas chromatography-mass spectrometry (GC-MS) analyses, the structure of the triglyceride was completely determined.

Synthesis of Triacylglycerol

The synthesis of triacylglycerol was based on the method of Besra et al. (Besra, G. S. et al. (1993) Chem. Phys. Lipids 66:23-34). Briefly, the acetylenic carboxylic acid (1) and trimethylsilyl chloride (0.1 equivalent) in anhydrous methanol were mixed at room temperature for 12 hours. The reaction was evaporated to dryness to yield the pure methyl ester product (2) as confirmed by thin layer chromatography (TLC) and $^1H/^{13}C$-NMR analysis and was used directly in the next step without further purification. The carboxylic acid methyl ester (2) was dissolved in diethyl ether and 2 equivalents of lithium aluminium hydride were added and the reaction was stirred at room temperature for 4 hours. The reaction was quenched with glacial acetic acid and the acetylenic alcohol product (3) was extracted with diethyl ether and water. The ethereal layer was recovered and washed with water and then brine, then concentrated to dryness. To a solution of the acetylenic alcohol (3) (1 equivalent) in hexamethylphosphoramide (HMPA), n-butyl lithium (2 equivalents) was added at 0° C. under nitrogen over a period of 30 min. The reaction was stirred at 0° C. for 20 min. 1-iodopentane (1.4 equivalent) was added and the reaction mixture was left to warm to ambient temperature and stirred for 20 hours. The reaction was quenched with the addition of saturated aqueous ammonium chloride and the product (4) was extracted with diethyl-ether. The product (4) was concentrated and purified by column chromatography using a petroleum ether-ethyl acetate gradient, monitored by TLC and characterized by $^1H/^{13}C$-NMR. A suspension of Lindlar's catalyst in dry benzene was saturated with hydrogen gas and cooled to 10° C. Then a solution of (4) in benzene and quinoline was added under a stream of nitrogen. The reaction mixture was stirred for 1 hour at 10° C. The reaction mixture was filtered, concentrated and the product (5) was purified by column chromatography using a petroleum ether-ethyl acetate gradient, monitored by TLC and characterized by $^1H/^{13}C$-NMR. A solution of (5) in dichloromethane (1 volume) was added to a stirring solution of pyridinium dichromate (4 equivalents) in dimethylformamide (DMF, 10 volumes). The reaction mixture was stirred for 2 days at room temperature. Water was added and the product (6) was extracted into dichloromethane, washed with brine and concentrated. The product (6) was purified by column chromatography and characterized by MS and $^1H/^{13}C$-NMR. The starting acid (6) was dissolved in dichloromethane/DMF and oxalyl chloride was added; the reaction mixture was then stirred at room temperature for 1 hour. The reaction mixture was evaporated and the crude acid chloride (7) was used in the next step. Glycerol (1 equivalent) in pyridine was added to the acid chloride (7) (3.3. equivalents) and the reaction mixture was left to stir overnight. Dichloromethane and water were added to the reaction mixture and the product was recovered in the organic layer and concentrated. The synthetic triacylglycerol was purified by column chromatography using increasing methanol in chloroform, monitored by TLC and characterized by MS, and $^1H/^{13}C$-NMR analyses. All indicated structures are shown in FIG. 6.

Thp1 Cell Assay

Thp1 cells were used as an immunological screen to characterize properties of the isolated lipid fractions of *M. vaccae* in terms of IL-12p40 and IL-10 secretion. Thp1 cells (ATCC, Teddington, UK) were differentiated overnight with 1.2% DMSO (Cat. No. D-5879; Sigma-Aldrich, Gillingham, UK) in culture media containing RPMI 1640 medium containing 20 mM Hepes buffer without L-glutamine (Cat. No. 42402-016; Gibco BRL, Grand Island, N.Y., USA), containing 10% fetal calf serum (Cat. No. 10106-169; Gibco BRLBRL), and 2 mM L-glutamine (Cat. no. 25030-024; Gibco BRLBRL). Cells were washed, counted and resuspended at a concentration of $2\times10^6$/ml. Cells were stimulated in vitro with isolated lipid fractions of *M. vaccae* at 37° C. and 5% $CO_2$. Supernatants were collected after 24 or 48 hours and cytokine concentrations were measured using commercially available ELISA kits (R&D Systems, Abingdon, UK). For experimental timeline, see FIG. 7, experiment 1.

Murine Model of Allergic Pulmonary Inflammation: Prevention Studies

Mice were treated subcutaneously on day −21 with either *M. vaccae* (0.1 mg in 100 µl of sterile saline), *M. vaccae* lipid preparation (1, 2, or 5 µg in 100 µl of buffer) or with sterile buffer alone. On days 0 and 12, mice were sensitized by intraperitoneal (i.p.) injection of 10 µg chicken egg ovalbumin (Grade V, Sigma-Aldrich, UK) in 100 µl of alum gel (AMS, Abingdon, UK). On days 19 and 21, mice were challenged intratracheally (i.t.) with 50 µl of 10 µg/ml ovalbumin in sterile saline solution (FIG. 7, Experiments 2-4).

Murine Model of Allergic Pulmonary Inflammation: Treatment Studies

In separate studies, 3 weeks prior to treatment with *M. vaccae* (0.1 mg in 100 µl of sterile saline), *M. vaccae* lipid preparation (5 µg in 100 µl of buffer) or with sterile buffer alone, animals received two earlier ovalbumin and alum injections 12 days apart (on days −42 and −30) to determine the therapeutic potential of treatment with *M. vaccae* and its lipid preparations (FIG. 7, Experiments 5 and 6). In some experiments the effects of different doses of *M. vaccae* lipid preparation (5 µg, 2 µg, 1 µg and 0.1 µg) were investigated. Mice were sacrificed 24 hours after the second i.t. antigen challenge by i.p. injection of sodium pentobarbital (240 mg/kg, Animal Care, York, UK). The trachea was cannulated and the BAL fluid was collected by washing three times with 0.3 ml of RPMI supplemented with 50 U/ml penicillin and 50 µg/ml streptomycin (Invitrogen). The number of cells recovered was determined using a Neubauer chamber. Differential cell counts for each BAL sample were obtained from slide cytospin (Cytospin 3, Shandon Scientific, Cheshire, UK) stained with Wright-Giemsa (Sigma-Aldrich). A differential count of 200 cells was performed using standard histological criteria. The remaining BAL fluid was centrifuged and the supernatant stored at −20° C. for cytokine analysis. Concentrations of IL-10 and IL-5 were measured using commercially available ELISA kits.

In Vitro Splenocyte Culture

Spleens from mice from each treatment group were pooled and a single cell suspension was prepared. Erythrocytes were removed by hypotonic lysis. Cells were washed and resuspended in culture media containing RPMI, 10% fetal calf serum, 2 mM glutamine, 50 U/ml penicillin and 50 µg/ml streptomycin. Splenocytes ($10\times10^6$/ml) were stimulated in vitro with phosphate-buffered saline (PBS; Invitrogen), ovalbumin (50 µg/ml) for antigen-specific stimulation, and with plate-bound anti-CD3 (0.5 µg/ml, Pharmingen, Oxford, UK) for polyclonal activation of T cells. Supernatants were collected 72 hours later for analysis of cytokine concentrations. Concentrations of IL-10, IL-5 and IFN-γ were measured using commercially available ELISA kits.

Synthesis of 10(Z)-hexadecenoic acid; (10Z)-hexadec-10-enoic acid (CAS No. 2511-97-9)

Unless otherwise noted, reagents were obtained commercially and used without further purification. Dichloromethane ($CH_2Cl_2$) was distilled over calcium hydride ($CaH_2$) under a nitrogen atmosphere. Tetrahydrofuran (THF;

(CH$_2$)$_4$O) was distilled from sodium-benzophenone under a nitrogen atmosphere. Thin-layer chromatography analysis of reaction mixtures was performed on Dynamic Adsorbents, Inc., silica gel F-254 TLC plates. Flash chromatography was carried out on Zeoprep 60 ECO silica gel. $^1$H spectra were recorded with a Varian INOVA 500 spectrometer. Compounds were detected by monitoring UV absorbance at 254 nm.

To a 5 mL sealed tube containing 1-heptene (0.50 mL, 3.55 mmol), methyl 10-undecenoate (0.080 mL, 0.36 mmol) and 0.35 mL THF was added to a Grubbs Z-selective metathesis catalyst (2.2 mg, 3.48 µmol, Sigma-Aldrich, Cat. No. 771082). The reaction was stirred at 45° C. for 8 h before cooling to room temperature. The slurry was filtrated through a short plug of silica gel and concentrated. The obtained oil was dissolved in 1.0 mL THF. The solution was cooled to 0° C., then 9-borabicyclo[3.3.1]nonane (9-BBN) solution in THF (1.28 mL, 0.50 M, 0.64 mmol) was added. After 2 h stirring at 0° C., the reaction was quenched with 60 µL EtOH, then 1.5 mL pH 7 potassium phosphate buffer and 1.5 mL 30% H$_2$O$_2$. The mixture was stirred at room temperature for 12 h, then extracted with 5 mL EtOAc three times. The combined organic layers were washed with 4 mL saturated Na$_2$S$_2$O$_3$ and 3 mL brine, then dried over Na$_2$SO$_4$, filtered and concentrated. To the crude oil in 1.0 mL THF was added LiOH monohydrate (38 mg, 0.90 mmol) in 1.0 mL water. After 2 h, the reaction solution was cooled to 0° C. before addition of 0.91 mL 1.0 N HCl. After being concentrated under reduced pressure, the aqueous solution was saturated with NaCl and extracted with 3 mL dichloromethane three times. The combined organic layers were dried over Na$_2$SO$_4$, filtered and concentrated. Purification by flash chromatography (2:1:1 hexanes/dichloromethane/diethyl ether) provided (10Z)-hexadec-10-enoic acid (0.022 g, 90%) as a colourless oil. $^1$H NMR (500 MHz, CDCl$_3$): δ 5.48-5.22 (m, 2H), 2.35 (t, J=7.5 Hz, 2H), 2.01 (q, J=6.6 Hz, 4H), 1.63 (p, J=7.4 Hz, 2H), 1.35-1.15 (m, 16H), 0.88 (t, J=6.9 Hz, 3H).

Murine Peritoneal Macrophage Isolation and Screening

Murine peritoneal macrophages were isolated as previously described (Zhang, X. et al. (2008)). Briefly, mice received one 1 ml i.p. injection of 3% thioglycollate medium (Cat. No. 9000-294, VWR, Radnor, Pa., USA). Ninety-six hours later, macrophages were collected in DPBS (Cat. No. 14190136, Invitrogen, Carlsbad, Calif., USA). Cells were centrifuged and resuspended in DMEM/F-12 (Cat. No. 10565018, Invitrogen) supplemented to be 10% (v/v) fetal bovine serum (Cat. No. 16000036, Invitrogen) and 1% penicillin/streptomycin (Cat. No. 15140148, Invitrogen). One mouse yielded enough cells for one experimental replicate. 1×10$^5$ cells/well were allowed to adhere for 1.5 h before being washed with DPBS. 10(Z)-hexadecenoic acid was dissolved in DMEM/F-12 with 0.5% (v/v) dimethyl sulfoxide (Cat. No. D8418, Sigma-Aldrich). The macrophages were incubated with either 10(Z)-hexadecenoic acid (0.4 µM, 4 µM, 20 µM, 100 µM, 500 µM, 1000 µM) or DMEM/F-12 for 1 h before being stimulated with 1 µg/ml lipopolysaccharide (serotype 0127:B8, Sigma-Aldrich, St. Louis, Mo., USA). Culture supernatants were collected at 6, 12, and 24 h post-stimulation.

Cytokine Measurements

Cell culture supernatants from freshly isolated peritoneal macrophages were diluted 1:200, and IL-6 was measured using sandwiched ELISA (Cat. No. 431304, Biolegend, San Diego, Calif., USA). All samples were measured in duplicate.

Cytotoxicity Assay

Cytotoxicity was determined using the sulforhodamine B (SRB) colorimetric assay, as previously described (Vichai and Kirtikara, 2006). Briefly, without removing the culture media, cells were fixed by adding cold trichloroacetic acid and incubated at 4° C. for 1 h. The plates were washed with slow-running tap water and set out to dry overnight. Then, 0.057% SRB (Cat. No. AC333130050, Fisher, Pittsburgh, Pa., USA), solubilized in 10 mMTris (Cat. No. BP153, Fisher), was added to each well. After 30 min, plates were washed with 1% acetic acid and set out to dry overnight. SRB was measured at 490 nm on a Synergy HT microplate reader (Part Number 7091000, Biotek, Winooski, Vt., USA). Cell viability was expressed as the ratio of experimental and control growth.

Ligands

Rosiglitazone, troglitazone, and WY14643 were obtained from Alexis Biochemicals (San Diego, Calif., USA); ATRA and AM580 from Sigma-Aldrich. In addition, GW9662 was a gift from T. M. Willson (GlaxoSmithKline, Brentford, United Kingdom).

Statistical Analysis

Results are represented as means±SEM. Data were subjected to a normality test and one-way ANOVA or Student's t-tests were performed as appropriate. A two-tailed p value ≤0.05 was considered significant.

What is claimed is:

1. A method of treating sepsis and/or preventing or treating post-sepsis syndrome comprising administering a therapeutically effective amount of 10(Z)-hexadecenoic acid to a patient in need of such treatment.

2. The method of claim 1, wherein the 10(Z)-hexadecenoic acid is administered via intravenous injection.

3. The method of claim 1, wherein the fatty acid molecule is administered via the intratracheal route.

* * * * *